(12) United States Patent  (10) Patent No.: US 6,726,829 B2
Trozera  (45) Date of Patent: Apr. 27, 2004

(54) METHOD OF MANUFACTURING A STENT (75) Inventor: Thomas Trozera, Del Mar, CA (US)

(73) Assignee: SciMed Life Systems, Inc., Maple Grove, MN (US)

( * ) Notice: Subject to any disclaimer, the term of this patent is extended or adjusted under 35 U.S.C. 154(b) by 217 days.

(21) Appl. No.: 10/004,337

(22) Filed: Nov. 1, 2001

(65) Prior Publication Data

US 2002/0038767 A1 Apr. 4, 2002

Related U.S. Application Data (60) Continuation-in-part of application No. 09/246,180, filed on Feb. 4, 1999, now Pat. No. 6,545,748, and a continuation-in-part of application No. 08/956,672, filed on Oct. 23, 1997, now Pat. No. 6,475,233, which is a division of application No. 08/835,015, filed on Apr. 8, 1997, now Pat. No. 5,902,475.

(51) Int. Cl.[7] ............................. C25F 3/00; C25D 5/02; C25D 5/34; C25D 5/48; B32B 1/08
(52) U.S. Cl. ..................... 205/655; 205/118; 205/151; 205/205; 205/209; 205/210; 205/212; 205/218; 205/221; 205/223; 205/224; 205/229; 216/8; 216/9; 216/10; 216/49; 216/53; 216/56; 216/67; 216/75; 216/83; 216/100
(58) Field of Search ............................. 205/151, 209, 205/210, 212, 218, 221, 223, 224, 229, 655, 118, 135, 205; 216/8–10, 33–35, 49, 52–53, 56, 67, 75, 83, 95, 100, 105

(56) References Cited

U.S. PATENT DOCUMENTS 2,170,896 A   8/1939   Henderson ...................... 95/73
2,288,352 A   6/1942   Henderson ...................... 95/73
3,573,045 A   3/1971   Lemelson ....................... 96/27
3,689,154 A   9/1972   Swain et al. ................... 355/97

(List continued on next page.)

FOREIGN PATENT DOCUMENTS

EP   0 709 067 A2   1/1996
EP   0780485   *  6/1997

OTHER PUBLICATIONS

U.S. patent application Ser. No. 10/098,785, Trozera, filed Mar. 13, 2002.
U.S. patent application Ser. No. 10/361,915, Trozera, filed Feb. 10, 2003.
U.S. patent application Ser. No. 08/835,015, Trozera et al., filed Apr. 8, 1997.
U.S. patent application Ser. No. 08/956,672, Trozera, filed Oct. 23, 1997.
U.S. patent application Ser. No. 09/246,180, Trozera, filed Feb. 4, 1999.

Primary Examiner—Patrick Ryan
Assistant Examiner—Thomas H Parsons
(74) Attorney, Agent, or Firm—Vidas, Arrett & Steinkraus (57) ABSTRACT Disclosed herewithin is an apparatus for fabricating a stent which involves processing a tubular member whereby no connection points to join the edges of a flat pattern are necessary. The process includes the steps of: a) preparing the surface of a tubular member, b) coating the outside surface of the tubular member with a photo-sensitive resist material, c) placing the tubular member in an apparatus designed to simultaneously rotate the tubular member while passing a specially configured photographic frame negative between a light source and the tubular member, d) exposing the tubular member to a photoresist developer, e) rinsing the excess developer and uncured resist from the exposed tubular member, f) sealing the inner lumen of the tubular member, and g) treating the tubular member with a chemical or electro-chemical process to remove uncovered metal. By modifying the photographic negative, this process can be employed to fabricate a virtually unlimited number of stent designs and configurations.

50 Claims, 7 Drawing Sheets

U.S. PATENT DOCUMENTS

| | | | |
|---|---|---|---|
| 3,694,080 A | 9/1972 | Malsky | 355/86 |
| 4,102,734 A | 7/1978 | Schiffman | 156/659 |
| 4,389,116 A | 6/1983 | Vogel | 355/85 |
| 4,733,665 A | 3/1988 | Palmaz | 128/343 |
| 4,739,762 A | 4/1988 | Palmaz | 606/194 |
| 4,776,337 A | 10/1988 | Palmaz | 128/343 |
| 4,994,071 A | 2/1991 | MacGregor | 606/194 |
| 5,019,090 A | 5/1991 | Pinchuk | 606/194 |
| 5,037,392 A | 8/1991 | Hillstead | 606/96 |
| 5,092,877 A | 3/1992 | Pinchuk | 623/1 |
| 5,102,417 A | 4/1992 | Palmaz | 606/195 |
| 5,104,404 A | 4/1992 | Wolff | 623/1 |
| 5,167,614 A | 12/1992 | Tessmann et al. | 604/8 |
| 5,192,297 A | 3/1993 | Hull | 606/195 |
| 5,192,307 A | 3/1993 | Wall | 623/1 |
| 5,195,984 A | 3/1993 | Schatz | 606/195 |
| 5,222,971 A | 6/1993 | Willard et al. | 606/158 |
| 5,226,913 A | 7/1993 | Pinchuk | 623/1 |
| 5,266,073 A | 11/1993 | Wall | 623/1 |
| 5,282,823 A | 2/1994 | Schwartz et al. | 606/198 |
| 5,304,200 A | 4/1994 | Spaulding | 606/198 |
| 5,306,294 A | 4/1994 | Winston et al. | 623/1 |
| 5,354,308 A | 10/1994 | Simon et al. | 606/198 |
| 5,395,390 A | 3/1995 | Simon et al. | 606/198 |
| 5,397,355 A | 3/1995 | Marin et al. | 623/12 |
| 5,405,377 A | 4/1995 | Cragg | 623/1 |
| 5,411,549 A | 5/1995 | Peters | 623/1 |
| 5,411,551 A | 5/1995 | Winston et al. | 623/1 |
| 5,421,955 A | 6/1995 | Lau et al. | 216/48 |
| 5,423,885 A | 6/1995 | Williams | 623/1 |
| 5,443,496 A | 8/1995 | Schwartz et al. | 623/1 |
| 5,449,372 A | 9/1995 | Schmaltz et al. | 606/198 |
| 5,449,373 A | 9/1995 | Pinchasik et al. | 606/198 |
| 5,464,650 A | 11/1995 | Berg et al. | 427/2.3 |
| 5,514,154 A | 5/1996 | Lau et al. | 606/195 |
| 5,527,354 A | 6/1996 | Fontaine et al. | 623/1 |
| 5,562,728 A | 10/1996 | Lazarus et al. | 623/1 |
| 5,624,508 A | 4/1997 | Flomenblit et al. | 148/510 |
| 5,628,787 A | 5/1997 | Mayer | 623/1 |
| 5,707,387 A | 1/1998 | Wijay | 606/194 |
| 5,718,713 A | 2/1998 | Frantzen | 606/198 |
| 5,733,326 A | 3/1998 | Tomonto et al. | 623/1 |
| 5,741,429 A | 4/1998 | Donadio, III et al. | 216/8 |
| 5,769,883 A | 6/1998 | Buscemi et al. | 623/1 |
| 5,780,807 A | 7/1998 | Saunders | 219/121.71 |
| 5,843,117 A | 12/1998 | Alt et al. | 606/194 |
| 5,902,475 A | 5/1999 | Trozera et al. | 205/655 |
| 5,907,893 A | 6/1999 | Zadno-Azizi et al. | 29/6.1 |
| 5,922,020 A | 7/1999 | Klein et al. | 623/1 |
| 5,941,895 A | 8/1999 | Myler et al. | 606/195 |
| 5,957,971 A | 9/1999 | Schwartz | 623/1 |
| 6,019,784 A | 2/2000 | Hines | 623/1 |
| 6,027,863 A | 2/2000 | Donadio, III | 430/320 |
| 6,107,004 A | 8/2000 | Donadio, III | 430/320 |
| 6,197,013 B1 | 3/2001 | Reed et al. | 604/509 |
| 6,291,502 B1 * | 9/2001 | Weichert et al. | 514/400 |
| 6,419,693 B1 | 7/2002 | Fariabi | 623/1.18 |

* cited by examiner

METHOD OF MANUFACTURING A STENT

PRIOR APPLICATIONS

This application is a continuation-in-part of application Ser. No. 08/956,672 filed on Oct. 23, 1997, now U.S. Pat. No. 6,475,233, issued Nov. 5, 2002 and Ser. No. 09/246,180 filed on Feb. 04, 1999, now U.S. 6,545,748, issued Apr. 8, 2002 which is a divisional of Ser. No. 08/835,015 filed on Apr. 8, 1997, now U.S. Pat. No. 5,902,475.

FIELD OF THE INVENTION

In general, the present invention relates to percutaneous transluminal devices and methods which are used to treat obstructed (sclerotic) vessel lumina in humans. In particular, the present invention is an improved method for fabricating stents or prostheses. In addition, the improved method employs a novel apparatus.

BACKGROUND OF THE INVENTION

Cardiovascular disease is commonly accepted as being one of the most serious health risks facing our society today. Diseased and obstructed coronary arteries can restrict the flow of blood and cause tissue ischemia and necrosis. While the exact etiology of sclerotic cardiovascular disease is still in question, the treatment of narrowed coronary arteries is more defined. Surgical construction of coronary artery bypass grafts (CABG) is often the method of choice when there are several diseased segments in one or multiple arteries. Conventional open heart surgery is, of course, very invasive and traumatic for patients undergoing such treatment. In many cases, less traumatic, alternative methods are available for treating cardiovascular disease percutaneously. These alternate treatment methods generally employ various types of balloons (angioplasty) or excising devices (atherectomy) to remodel or debulk diseased vessel segments. A further alternative treatment method involves percutaneous, intraluminal installation of one or more expandable, tubular stents or prostheses in sclerotic lesions. Intraluminal endovascular prosthetic grafting is an alternative to conventional vascular surgery. Intraluminal endovascular grafting involves the percutaneous insertion into a blood vessel of a tubular prosthetic graft and its delivery via a catheter to the desired location within the vascular system. The alternative approach to percutaneous revascularization is the surgical placement of vein, artery, or other by-pass segments from the aorta onto the coronary artery, requiring open heart surgery, and significant morbidity and mortality. Advantages of the percutaneous revascularization method over conventional vascular surgery include obviating the need for surgically exposing, removing, replacing, or by-passing the defective blood vessel, including heart-lung by-pass, opening the chest, and general anesthesia.

Stents or prostheses are known in the art as implants which function to maintain patency of a body lumen in humans and especially to such implants for use in blood vessels. They are typically formed of a cylindrical metal mesh which can expand when pressure is internally applied. Alternatively, they can be formed of wire wrapped into a cylindrical shape. The present invention relates to an improved method of manufacturing stents.

Stents or prostheses can be used in a variety of tubular structures in the body including, but not limited to, arteries and veins, ureters, common bile ducts, and the like. Stents are used to expand a vascular lumen or to maintain its patency after angioplasty or atherectomy procedures, overlie an aortic dissecting aneurysm, tack dissections to the vessel wall, eliminate the risk of occlusion caused by flaps resulting from the intimal tears associated with primary interventional procedure, or prevent elastic recoil of the vessel.

Stents may be utilized after atherectomy, which excises plaque, or cutting balloon angioplasty, which scores the arterial wall prior to dilatation, to maintain acute and long-term patency of the vessel.

Stents may be utilized in by-pass grafts as well, to maintain vessel patency. Stents can also be used to reinforce collapsing structures in the respiratory, biliary, urological, and other tracts.

As described in U.S. Pat. No. 4,776,337 issued to Palmaz, the cylindrical metal mesh shape is produced by laser cutting a thin walled metal tube. A laser is used to cut away all but the lines and curves of the mesh. The method of U.S. Pat. No. 4,776,337 is applicable for relatively large mesh shapes and for meshes whose lines are relatively wide. However, for more delicate and/or intricate shapes, the spot size of the laser is too large.

European Patent Application EP 0 709 067 A2 describes a stent fabrication method of preparing a flat pattern design, cutting the pattern in the flat sheet, deforming the sheet to cause the edges to touch, connecting the edges at least at one point usually by a welding process, and then polishing the finished product. The disadvantage of this process is that the flat sheet must be deformed to form the final tubular configuration and that there is a longitudinal attachment point which provides a discontinuous outer contour. In addition, this process requires several critical manufacturing steps which are eliminated by the present invention.

U.S. Pat. Nos. 5,514,154 and 5,421,955 describe a stent manufacturing process utilizing a computer controlled laser to selectively remove an etchant-resistant coating forming a design resembling a stent. The use of a laser to selectively remove the etchant-resistant coating is a relatively expensive and complicated process. The laser must be linked to a computer controlled X-Y movement system that must precisely control the rotation and movement of the laser for stent fabrication. Variances in this process will transcend into variability in the fabricated stent. The present invention neither requires the use of an expensive laser system nor the complex movement system.

It is, therefore, an object of the present invention to provide an apparatus to facilitate a stent fabrication method which can produce stents with relatively intricate, delicate, and detailed designs from a tubular member which negates the disadvantages of the prior designs.

In addition, it is a further object of the present invention to provide an apparatus to facilitate a method of fabricating a stent which involves processing a tubular member whereby no connection points to join the edges of a flat pattern are necessary.

SUMMARY OF THE INVENTION

The present invention involves an apparatus to facilitate the method of fabricating a stent by processing a tubular member. The stent production process is a multi-step, photolithographic process in which a small-diameter metal tube is coated with photoresist, which is photolithographically patterned and developed, after which the metal tube is chemically etched to form a tubular stent with apertures corresponding to the photoresist pattern. During the fabrication process, the novel apparatus exposes a coated tubular member to a precise pattern of light (UV) dictated by a specifically designed film or mask which moves over the tubular member as it is rotated.

The method of manufacture includes the steps of first cleaning the tubular member with an appropriate solution. The tubular member is comprised from stainless steel, platinum, gold alloy, or a gold/platinum alloy, but a number of metallic elements can be employed.

Once the tubular member is cleansed of contaminates, the outer surface is uniformly coated with a photo-sensitive resist. Optionally, a coupling agent or surface treatment may be used to facilitate the bonding of the photo-sensitive resist to the tubular member. The coupling agent or surface treatment is not essential in that some tubular member compositions bond directly to the photo-sensitive resist solution without the need for a coupling agent.

This coated tubular member is then placed in the apparatus designed to mount or rotate the tubular member while the coated tubular member is exposed to designated pattern of light preferably in the ultraviolet (UV) range. The apparatus controls the exposure of the coated tubular member by utilizing a photographic film or mask with a specified imprinted configuration, transferring the light in the specified pattern to the coated tubular member. The light waves can either activate the photo-sensitive coating causing the areas where the light is present to expose and cross-link the photo-sensitive material or can de-activate a photo-sensitive material causing the unexposed areas to remain intact while the exposed areas can be easily removed. In the preferred embodiment, the photo-sensitive resist forms cross links where is it exposed to the light thus forming a pattern of hardened and cured polymer which mimics the particular stent design surrounded by uncured polymer. The film is adaptable to virtually an unlimited number of intricate stent designs. The process from the apparatus results in the tubular member having a discrete pattern of exposed photo-sensitive material with the remaining areas having unexposed photo-sensitive resist.

The exposed tubular member is immersed in a negative resist developer for a specified period of time. The developer removes the relatively soft, uncured photo-sensitive polymer and leaves behind the cured photo-sensitive resist which mimics the stent pattern. Thereafter, excess developer is removed from the tubular member by rinsing with an appropriate solvent. At this time, the entire tubular member is incubated for a specified period of time, allowing the remaining photo-sensitive resist polymer to fully cure (harden) and attach to the surface of the processed tubular member.

The prevent chemical or electro-chemical etching from occurring within the inside lumen of the tubular member, the lumen is appropriately sealed.

The processed tubular member is then exposed to a chemical etching process which removes uncovered metal from the tubular member, resulting in final tubular member or stent configuration.

This process can lend itself to virtually an unlimited number of stent designs and configurations. By modifying the film and employing the identical process one can fabricate a variety of stent designs.

The present invention will be understood and appreciate more fully from the following detailed description taken in conjunction with the drawings.

BRIEF DESCRIPTION OF THE DRAWINGS

FIG. 5 is a cross-sectional view of the tubular member of the present invention with the optional coupling agent engaged to the outside surface of the tubular member;

DESCRIPTION OF THE PREFERRED EMBODIMENT

Figure 1:
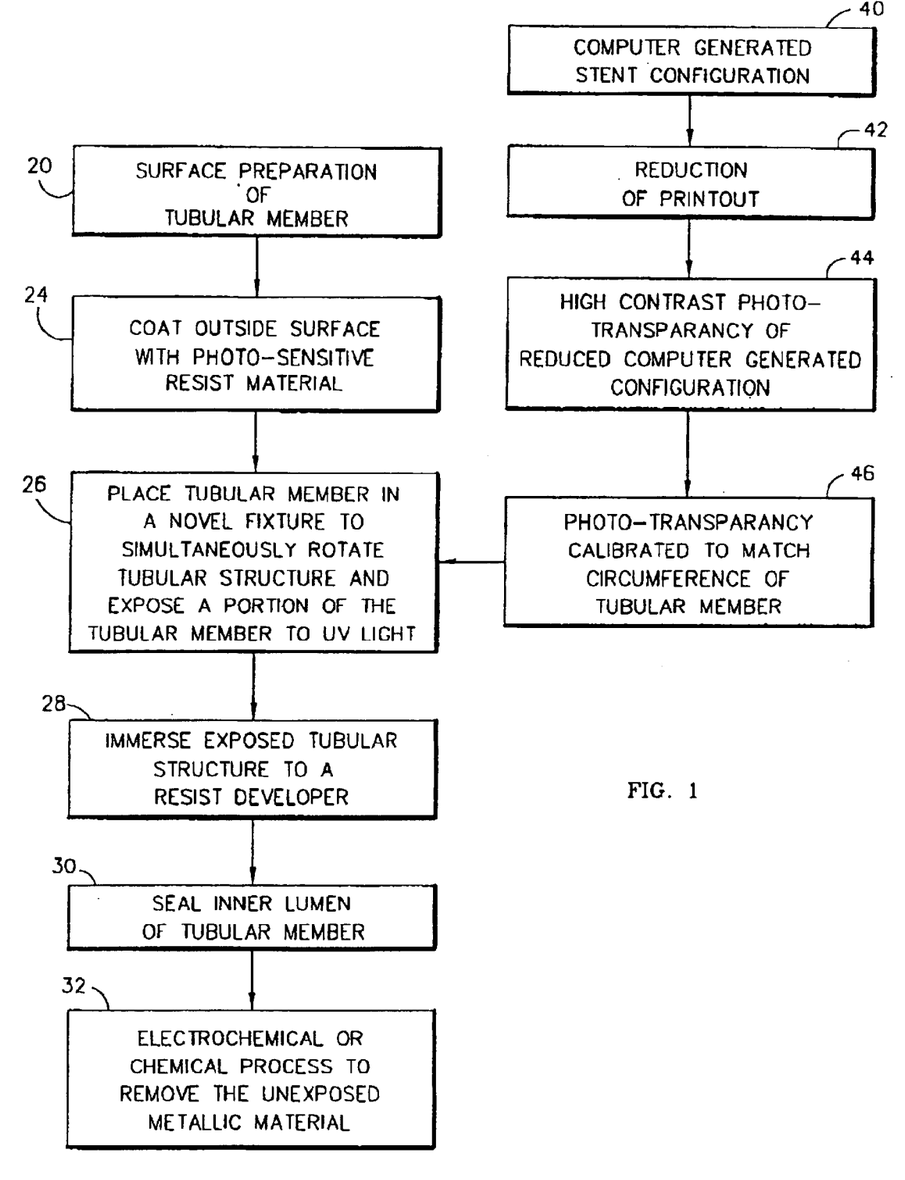
FIG. 1 is a general flow chart illustration of the stent fabrication method of the present invention.
Figure 2:
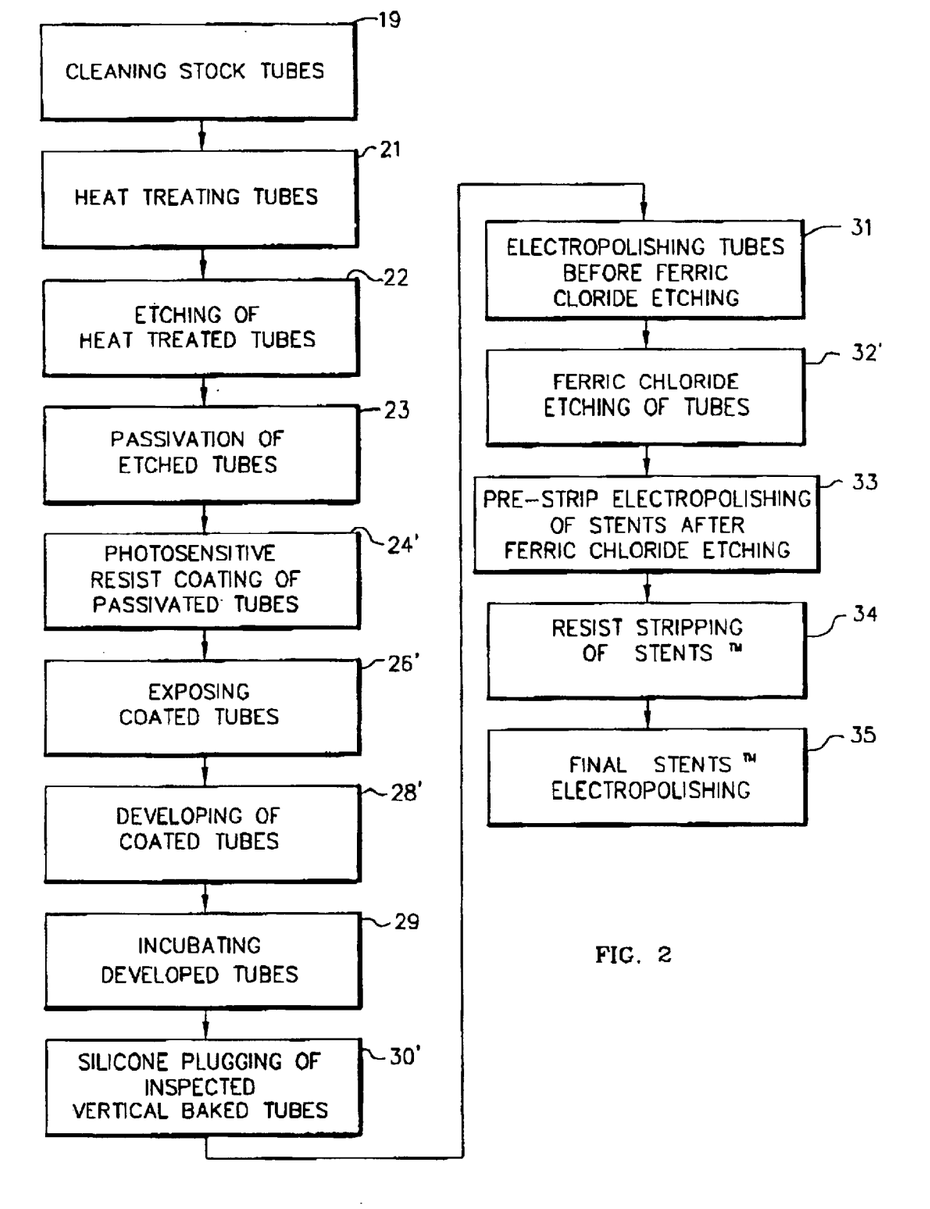
FIG. 2 is a detailed example flow chart illustration of the stent fabrication method of the present invention demonstrating the 316 stainless steel embodiment process.

Reference is now made to FIGS. 1 and 2, which illustrates the stent fabrication method of the present invention. FIG. 1 demonstrates a general stent fabrication process while FIG. 2 presents a more detailed 316 stainless steel example of the stent fabrication process.

The IVT stent production process is a multi-step, photo-lithographic process in which a small-diameter metal tube is coated with photoresist, which is photolithographically patterned and developed, after which the metal tube is chemically etched to form a tubular stent with apertures corresponding to the photoresist pattern. Flowcharts representing the processes in FIGS. 1 and 2 are described in more detail below.

In the stent fabrication method of the present invention, a drawing representing a stent is designed on a computer that generates a printout with the desired stent pattern presented in a flat format 40. The pattern of step 40 can be printed on any size printout, but generally must be reduced to fit the requirements of photographic film 42 and the dimensions of the desired stent design. After the drawing of the stent pattern is reduced, it is transferred onto a high contrast transparent film 44. The final step requires that the photo-transparent film be calibrated to match the circumference and dimensions of the tubular member employed in the fabrication process 46.

The tubular member can be any type of biocompatible materials, such as stainless steel, platinum, gold alloy or gold/platinum alloy, or a material which is plated with a biocompatible material. More specifically, candidates for stainless steel material for the tubular member include the 316 or 321 stainless steel classes, or radiopaque stainless steel alloys. The process of forming the tubular member is well known extrusion technology. It is preferable to have the tubular member relatively consistent in diameter, concentricity, thickness, and seamless.

To process the particular tubular member, is it preferable to clean and remove contaminates 20. More specifically, the raw stock tubes are sequentially cleaned in an ultrasonic bath. The tubes then are sequentially air-dried and heat dried in a heated oven under vacuum (step 19). The cleaned tubes are then heat treated in a furnace under vacuum (step 21) to achieve a yield strength of approximately 55 ksi. The surfaces of the heat-treated tubes are prepared for coating by electro-etching in a solution of Hydrite 4000 and water, under specific voltage, temperature, and time conditions. The pre-etched tubes are then examined under the microscope to assure surface quality characteristics (step 22).

The pre-etched tubes then are passivated by sequentially placing the etched tubes in a passivation solution, heated within a narrow temperature range for a specified time, placing the tubes in a water bath, and finally cleaning the tubes in methylene chloride (step 23). After the tubes are dried in a heated vacuum oven, one end of each tube is closed with a Teflon plug, and the tubes are coated with a photosensitive resist coating. The coated tubes then are vacuum degassed at a specified vacuum (pressure).

Dependent on the tubular member's material and the photo-sensitive resist material employed, a coupling agent or surface treatment may be necessary to enhance the adhesion of the photo-sensitive resist to the outer surface of the tubular member. Therefore, after the cleaning, etching process, and passivation of the raw tubular member, the outside surface of the tubular member is optionally coated with a coupling agent (not shown).

The tubular member may be given a plasma etch treatment prior to coating the outer surface with the photo-sensitive resist.

The processed tubular member is then coated with a photo-sensitive resist and degassed a second time (step 24 or 24').

Next, a novel apparatus is employed which exposes the resist coated to a specific pattern of UV light. The coated tubes are patterned by exposure using an automated exposing machine (step 26 or 26'). The automated exposing machine causes light to pass through the transparent portions of the negative and to impinge on the photoresist, thereby exposing and cross linking portions of the photoresist in a pattern that corresponds to these transparent portions of the negative.

The exposed tubes then are dipped into a developer solution by an automated developing machine (step 28 or 28'). The developed tubes then are placed in an oven and baked (step 29) to remove all traces of the developer and to firmly cross link the stent pattern on the tube surface.

The baked tubes are plugged with an un-cured liquid silicone rubber that is injected into the tube to completely fill its inner lumen (step 30 or 30'). The rubber is then cured slowly at three temperatures (25, 50 and 70 degrees C.) to minimize shrinkage and maintain adhesion to the inside wall of the tubes thereby creating a rubber mandrel. The rubber mandrel functions to prevent any etchant from penetrating the inner lumen of the tubular member. This process ensures that no etching occurs from the inside of the tubular member where no photoresist is present. If random etching was occurring from the inside of the tubular member, the particular stent design and physical strengths would be substantially compromised. The rubber mandrel also functions to provide a means to support the photoresist coated tubular members during the etching process. The plugged tubes then are electropolished prior to etching (step 31).

The electropolished tubes next are ferric-chloride etched (step 32 or 32'). In the etching process, the tubes are placed on an etching fixture that is positioned within a spray-etching compartment in which a finely atomized etchant is sprayed against the tubes. The tubes are rotated to ensure that the circumference surface is exposed to the etchant consistently and at a rate that creates a centrifugal force to prevent etchant from seeping between the photoresist material and the tubular member. The atomized droplets of etchant are controlled by controlling fluid pressure, air pressure cycle time, fluid flow rate, and temperature for each nozzle. The nozzle pressure and contact of the etchant on the tubes is rigorously controlled to further prevent etchant from seeping between the photoresist material and the tube material, which could cause weakening or complete destruction of the struts of the stent. After spraying of the etchant, the tubes are moved to a rinse chamber to rinse off the excess etchant.

Following the etching procedure, the stent is electropolished (step 33). In this step, each stent is manually processed through multiple steps in a heated solution to which an electrical current is applied to remove the remaining, unwanted metal.

The electropolished stent is resist stripped to remove any remaining photoresist material from the stent (step 34). In this step, the stents are placed in a beaker that contains a stripping solution and heated in a water bath until the resist material is dissolved off. This step is repeated a second time with a fresh stripping solution to ensure that all traces of the resist material is completely stripped from the stent.

After the resist material has been stripped away, the stents are electropolished a final time (step 35). The stents are placed in a heated etching solution that is subjected to a controlled voltage and current. The stents are placed in the electropolishing solution at specified angles, located in the solution, and held at a specific positions as required. The stents are then placed on an automated dipping machine that provides controlled movement within the electropolishing solution at a specified current, for a specified time, and for a specified number of dips. The stents then are inspected to ensure compliance with acceptance criteria.

Figure 3:
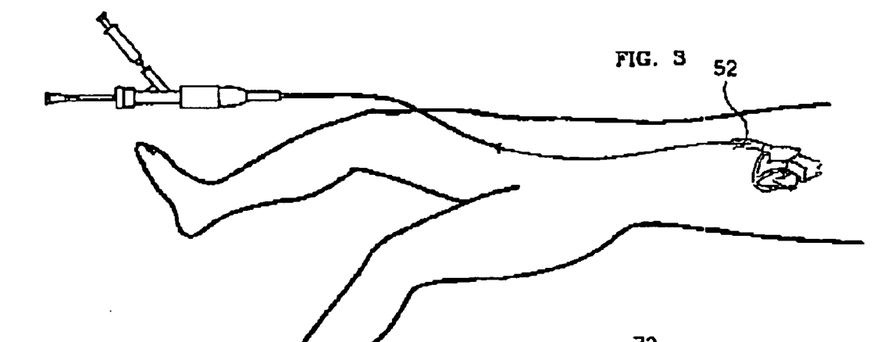
FIG. 3 is a schematic view of the finished stent of present invention in its intended operational environment.

FIG. 3 is a schematic view of the finished stent of present invention in its intended operational environment. A stent 52 resulting from the present invention can be used to treat atherosclerotic disease, prevent vessel recoil, overlie an aortic dissecting aneurysm, tack dissections to the vessel wall, and eliminate the risk of occlusion caused by flaps in both coronary native vessels and by-pass grafts.

Stents can also be used to reinforce collapsing structures in the respiratory, biliary, urological, and other tracts.

Figures 4, 5A, 5B, 6A, 6B:
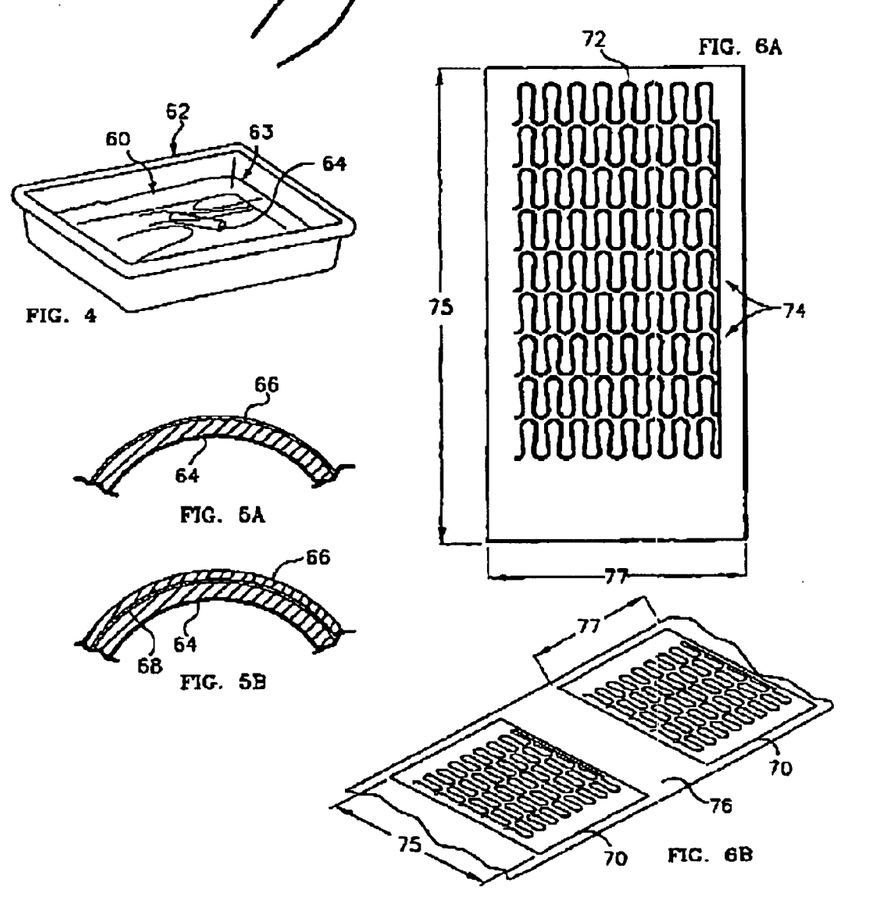
FIG. 4 is a schematic representation of the first cleaning step of the manufacturing process of the present invention.
FIG. 6A is a top view illustration of one frame of film with a stent configuration imprinted on the film.
FIG. 6B is a slanted lop view illustration of several frames on a sheet of film with a stent configuration imprinted on each frame.

For steps 20, 24, and 24', FIG. 4 demonstrates a simple means for exposing tubular member 64 to a cleaning solution 60, coupling agent 61, or the photo-sensitive resist 63 within a container 62. For example, Industroclean solvent detergent made by Amway Corporation is an example of suitable commercially available cleaning solution. The preferred procedure involves placing the raw stock tubes in an ultrasonic bath for sequential cleaning. The tubes then are sequentially air-dried and heat dried in a heated oven under vacuum (step 19) as shown in FIG. 2. The cleaned tubes are then heat treated in a furnace under vacuum (step 21) to achieve a yield strength of approximately 55 ksi. The surfaces of the heat-treated tubes are prepared for coating by electro-etching in a solution of Hydrite 4000 and water, under specific voltage, temperature, and time conditions. The pre-etched tubes are then examined under the microscope to assure surface quality characteristics (step 22).

A number of organo-silane coupling agents may be employed with the current invention process. Some examples of commercially available organo-silane coupling agents are vinyltriethoxysilane or methyltriethoxysilane made by Union Carbide and Z-6040 (containing glycidoxypropyltrimethoxysilane) or Z-6020 (containing aminoethylaminopropyltrimethoxysilane) made by Dow Corning. Probimide made by Olin Industries is an example of suitable commercially available photo-sensitive resist. If alternately a surface treatment is employed, a plasma apparatus, such as the March Plasmod maching produced by March Industries, can enhance the surface to facilitate adhesion of the photo-resist.

When exposing the tubular member 64 with some commercially available photo-sensitive resists 63, the thickness of the resist polymer layer is dependent upon the amount of exposure time and possibly, the method of exposure or other variables. One method that can be employed to control the thickness of the photo-sensitive resists is to uniformly draw the tubular member(s) 64 through a solution of photo-resist for a specified period of time to obtain the desired coating layer. Furthermore, it may be desirable to protect the internal lumen of the tubular member from the photo-sensitive resist polymer during the exposure process.

It should be obvious to the one skilled in the art that standard methods of subjecting one or more tubular members to a cleaning solution are commercially available and can be employed with the present invention. Furthermore, it should be obvious to one skilled in the art that standard methods of coating one or more tubular members with a coupling agent or photo-sensitive resist are commercially available and can be employed with the present invention. Having said this, subjecting tubular members of different metallic compositions may require different commercially available photo-sensitive resists or, if necessary, coupling agents.

FIG. 5A demonstrates a cross-section of the outer surface of tubular member 64 coated with a photo-sensitive resist 66. In this example, the adhesion properties between tubular member 64 and the resist 66 is robust enough to not require an intermediate coupling agent layer. For example, using class 316 or 321 stainless steel for the tubular member with Probimide made by Olin Industries is an example of a suitable photo-sensitive resist/tubular member combination that does not need a coupling agent. It should be recognized by the artisan that there are several classes of polymers that can be employed with the present invention to function as a protective coating.

FIG. 5B shows a cross-section of the outer surface of tubular member 64 coated with a photo-sensitive resist 66. Sandwiched between the tubular member 64 and resist 66 is a coupling agent 68. In this example, the adhesion properties requires the use of a coupling agent to facilitate and strengthen the bond between the tubular member 64 and the resist 66. For example, using gold alloy or platinum metal for the tubular member with Probimide photo-sensitive resist is an example of a combination that may need an organo-silane coupling agent to strengthen the bond between the tubular member and the resist.

FIGS. 6A and 6B show a preferred stent configuration imprinted on a transparent photographic film. The drawing of the pattern is generated on a computer program, reduced, and printed onto a transparent film. For example, a stress analysis program called ALGOR was used to develop the computer generated printouts. The printout is then sent to a film processing facility who reduces the printout and generates a precisely dimensioned negative. As discussed in more detail below, the dimensions of the negative must be calibrated to render a specific stent design. Because of regulations concerning patent drawings which prohibits large blackened areas, an explanation of the drawings used to represent the photographic film is necessary. In FIGS. 6A and 6B, the open (transparent) spaces which allow the UV light to pass through the film are represented as solid black areas and alternating loops 72. The white areas of the drawings 6A and 6B represent the exposed (black) areas of the film which will block the light (UV) from passing through the film and exposing the underlying areas to the light. The combined transparent spaces and solid black areas represent the particular stent design 74. An example of a suitable film that can be employed in the present invention is Kodak ALI-4 Accumax film made by Kodak Industries. The length 77 of stent imprint is directly equal (1 to 1) to the circumference of tubular member 64. The width 75 is equivalent to the working length of the processed stent. FIG. 6B shows the transparent photographic film 76 with multiple frames 70 of the preferred stent configuration.

Figures 7, 8, 9:
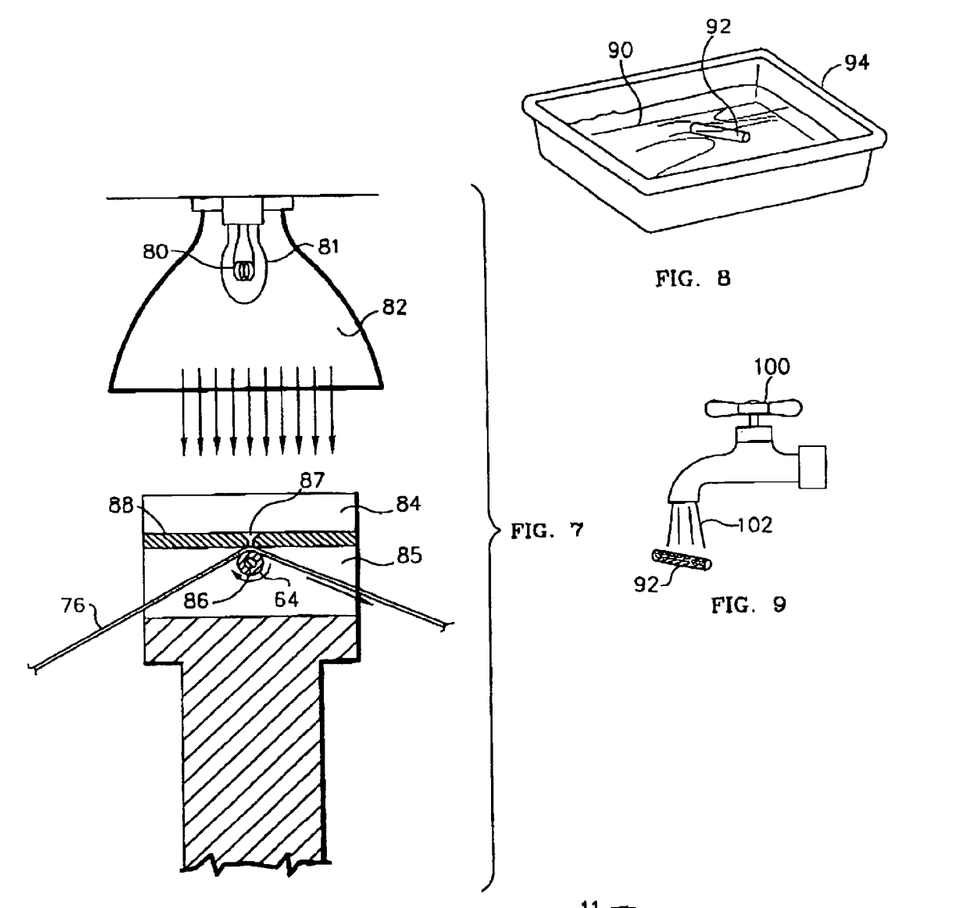
FIG. 7 is a side view illustration of the apparatus used to simultaneously rotate the coated tubular member, advance the film, and expose a portion of the outer surface of the tubular member to light.
FIG. 8 is a schematic representation of the processing step of immersing the coated tubular member expose to light in a negative resist developer to yield an unrefined stent.
FIG. 9 is a schematic representation of the processing step of rinsing the excess negative resist developer from the unrefined stent.

FIG. 7 shows sections of the apparatus including the lamp 82, with a specific wavelength such as in the ultraviolet range, laid-out in a typical configuration with sealed bulb 81 and filament 80 in an assembly. A regulating platform 84 comprises a base 85 with a top plate 88. A specially configured slit 87 centers the (ultraviolet) light into a narrow beam which reaches and penetrates the specific pattern of transparent film 76. Selected portions of the coated tubular member are illuminated with ultra-violet light which causes the exposed photo-resist to react and change its properties (cure and harden) and result in those portions remaining after electrochemical etching as the stent struts 118.

The platform also comprises a rotating member 86 engaged with tubular member 64. Rotating member 86 moves in conjunction with the film passing over the rotating tubular member.

For step 28 or 28', FIG. 8 demonstrates a simple means for exposing tubular member 92 to a negative resist developer 90, within a container 94. It should be recognized by the artisan that there are numerous commercially available solvents for selectively removing the unexposed photo-sensitive resist of polymeric protective coating. It should also be obvious to the artisan that standard methods of exposing one or more tubular members with a negative resist developer can be employed.

FIG. 9 is a representation of step 30 or 30' where a means 100 is used to remove unexposed photo-sensitive resist or protective polymeric coating and rinse excess negative resist developer or other selective solvents from the partially exposed tubular member 92 using an appropriate solvent 102. In the preferred embodiment, QZ3501 made by Olin Industries is an example of suitable commercially available solvent to rinse the excess negative resist developer.

Prior to the chemical etching process as described in more detail below, a polymeric mandrel or plug apparatus is positioned within the inside lumen of the tubular member 92 providing two functions. The mandrel or plug 95 can consist of a silicone type material that is molded and incubated within the lumen to create a fluid tight seal. This is an important step during the chemical etching process, for the inside surface of the tubular member must not be exposed to any etchant. Since there is no photo-resist on the inside surface of the tubular member, the etchant would randomly or uncontrollably remove metal from the inside of the tubular member out towards the outside surface. This would severely impact the design of the stent product as well as compromise integrity or quality of the finished product. The second function of the polymeric mandrel is to provide a means to support the tubular structure during the etching process.

Figure 10:
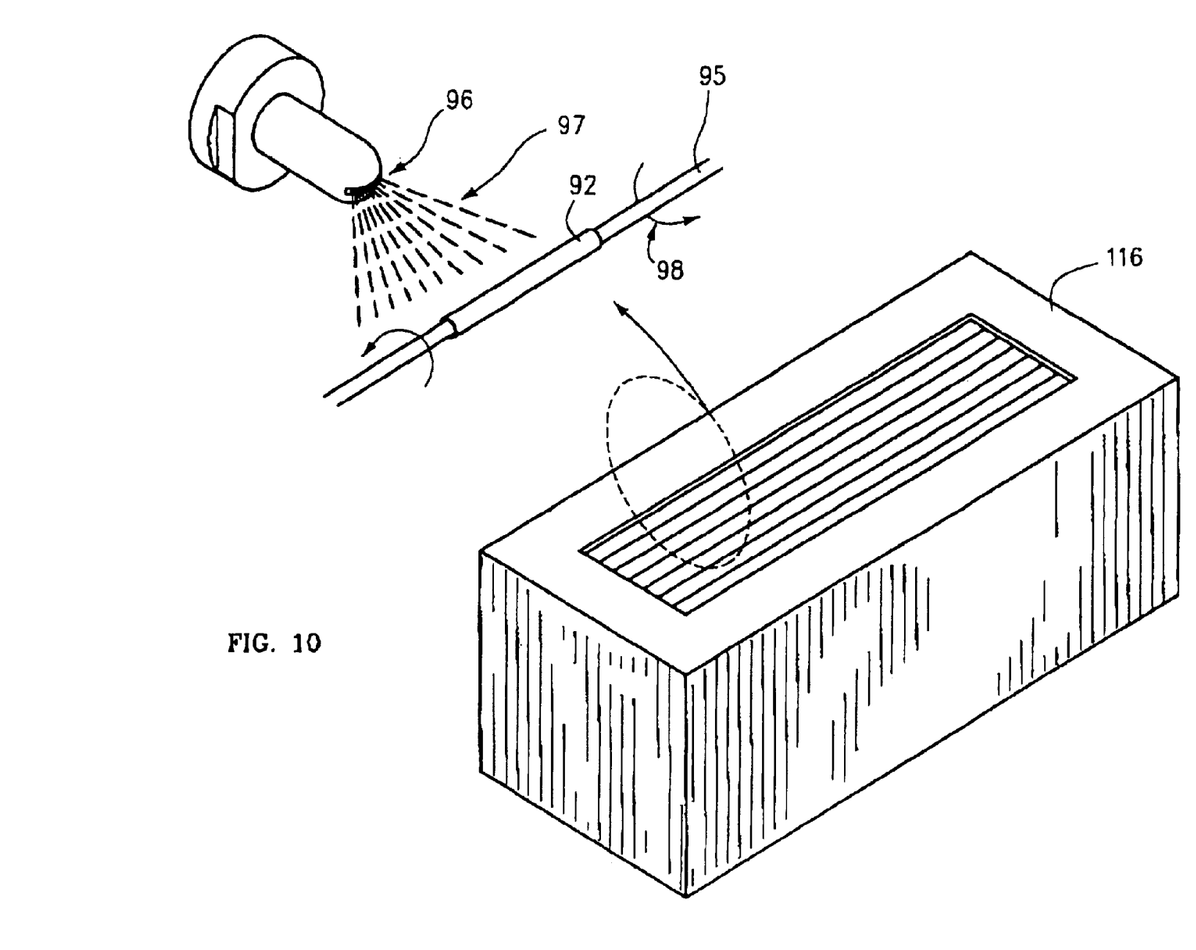
FIG. 10 is a schematic representation of the processing step of chemically or electro-chemically treating the unrefined stent to a finished stent.

FIG. 10 is a representation of step 32 or 32' where a chemical or electo-chemical means is employed to remove the unexposed metallic material from the exposed tubular member 92. Shown in FIG. 10 is an example of an electro-chemical solution contained with a processing etch apparatus 116. In one embodiment, a combination of phosphoric acid and sulfuric acids are employed to etch unexposed metallic material. Hydrite 4000 made by Hydrite Industries is an example of suitable commercially available chemical etching solution that contains the phosphoric and sulfuric acids. When employing a tubular member composed of stainless steel classes, the preferred chemical or electro-chemical etching solution comprises a solution of ferric chloride. If the tubular member is composed of a gold alloy or platinum, other chemical or electro-chemical etching solutions, such as potassium cyanide, aqua regia (hydrochloride and nitric acids), or sodium hypochloride Further referring to FIG. 10, the etching processes is shown in more detail. It is important that during the etching process, additional controls are enacted. By regulating the exposure of the etching solution to the metal substrate, under-cutting at the edges of the photo-resist is negated or minimized. This is accomplished by two independent but simultaneously conducted processes. The first process employs a unique nozzle design 96 which creates a mist or small droplet size 97 of the etching solution that is applied to the tubular member 92. This nozzle design also must uniformly provide the mist or small droplet size of etching solution over the entire length of the tubular member which results in a stent product. The second simultaneous process is rotating the tubular member 98 with a polymeric mandrel at a speed which creates centrifugal force, thereby causing the minute droplets not to pool within crevices in the coated tubular member but rather be separated from the tubular member at a constant rate. Using the two processes provides the additional controls during the etching process which is necessary for tubular members of the small size of stents.

If energization of the etchant solutions is desired, a negative charge can be supplied through a cathode (which is immersed in the etchant solution) to the positively charged electrode with is engaged to final tubular member 119 (of which both are immersed in the etchant solutions). Materials commonly employed as cathodes are platinum or gold. It should be obvious to one skilled in the art that standard methods of treating one or more tubular members with a electro-chemical means can be employed.

Figures 11, 12, 13:
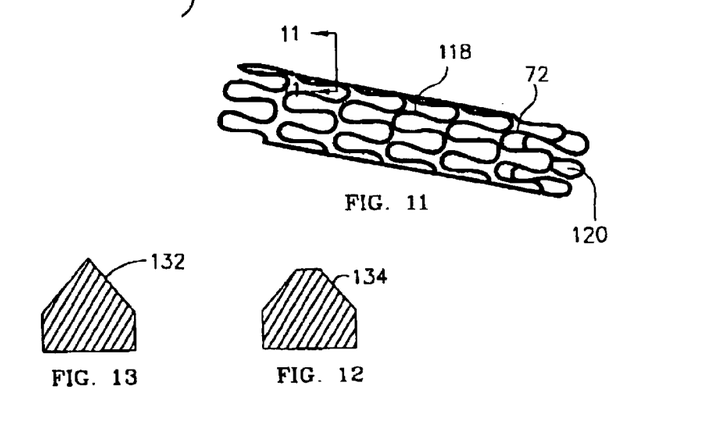
FIG. 11 is a perspective view of a stent resulting from the manufacturing process of the present invention.
FIG. 12 is a cross-sectional view of one configuration of the outer surface of a strut as seen along line 11—11 in FIG. 10 showing a trapezoidal protruding configuration that is directed radially from the longitudinal axis of the stent as a result of the present invention process.
FIG. 13 is a cross-sectional view of another configuration of the outer surface of a strut as seen along line 11—11 in FIG. 10 showing a triangular protruding configuration that is directed radially from the longitudinal axis of the stent as a result of the present invention process.

FIG. 11 is a representation of the preferred stent design 72 that results from the present invention method. The portions of the photoresist that were exposed to UV illumination and changed physical properties (cured and hardened) are retained during the electro-chemical process and remain intact as the struts or loops 118 of stent 72. The portions of the photoresist that were not exposed to UV illumination are removed during the electro-chemical process and result in open spaces 120. The structure resulting from a pattern of struts 118 and open spaces 120 comprises the desired stent configuration.

Figure 14:
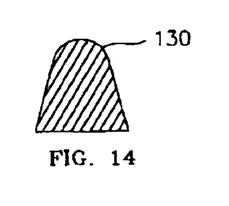
FIG. 14 is a cross-sectional view of another configuration of the outer surface of a strut as seen along line 11—11 in FIG. 10 showing a protrusion with a radius that is directed radially from the longitudinal axis of the stent as a result of the present invention process.

The present invention results in the preferred stent design 72 having specifically configured struts 118. FIGS. 12, 13, and 14 illustrate, in cross-section, three exemplary stent strut designs. As demonstrated in FIG. 12, the preferred stent design has the outer portion of the struts protruding in a trapezoidal configuration 134 which is directed radially from the longitudinal axis of the stent. The pattern of the preferred stent employs cross-section FIG. 12 and has a series of loops (U-shaped) 118 and a single backbone running along the length of the stent, thereby forming the basic scaffold of the stent design.

The pattern of FIGS. 11 and 12 can be formed of any size; a preferable size is between 0.035 thousandths to 0.100 thousandths in diameter when formed (crimped). The expanded or deployed diameter ranges from 2.0 mm to 8.0 mm with a preferred range for coronary applications of 2.5 mm to 6.0 mm. The length of the stent is virtually constant from its initial formation length to its length when expanded and ranges from 2 mm to 50 mm, with a preferred length for coronary applications of 5 mm to 20 mm.

In an alternate embodiment, the pattern of stent 72 is similar to that of FIGS. 11 and 12 but differs in the outer portion of the strut comprising a triangular configuration 132 (FIG. 12) where the point of the triangle is directed radially from the longitudinal axis of the stent. In an another alternate embodiment, the pattern of stent 72 is similar to that of FIGS. 11 and 12 but differs in the outer portion of the strut comprising an extended base with a radius 130 (FIG. 14) directly radially from the longitudinal axis of the stent.

Finally, the stent 72 can be polished to remove any excess material not properly removed by the process. The polishing can be performed mechanically, by rubbing a polishing stick having diamond dust on its outside inside the stent 72. Alternatively, an additional electro-polishing step can be utilized.

Figures 15, 16:
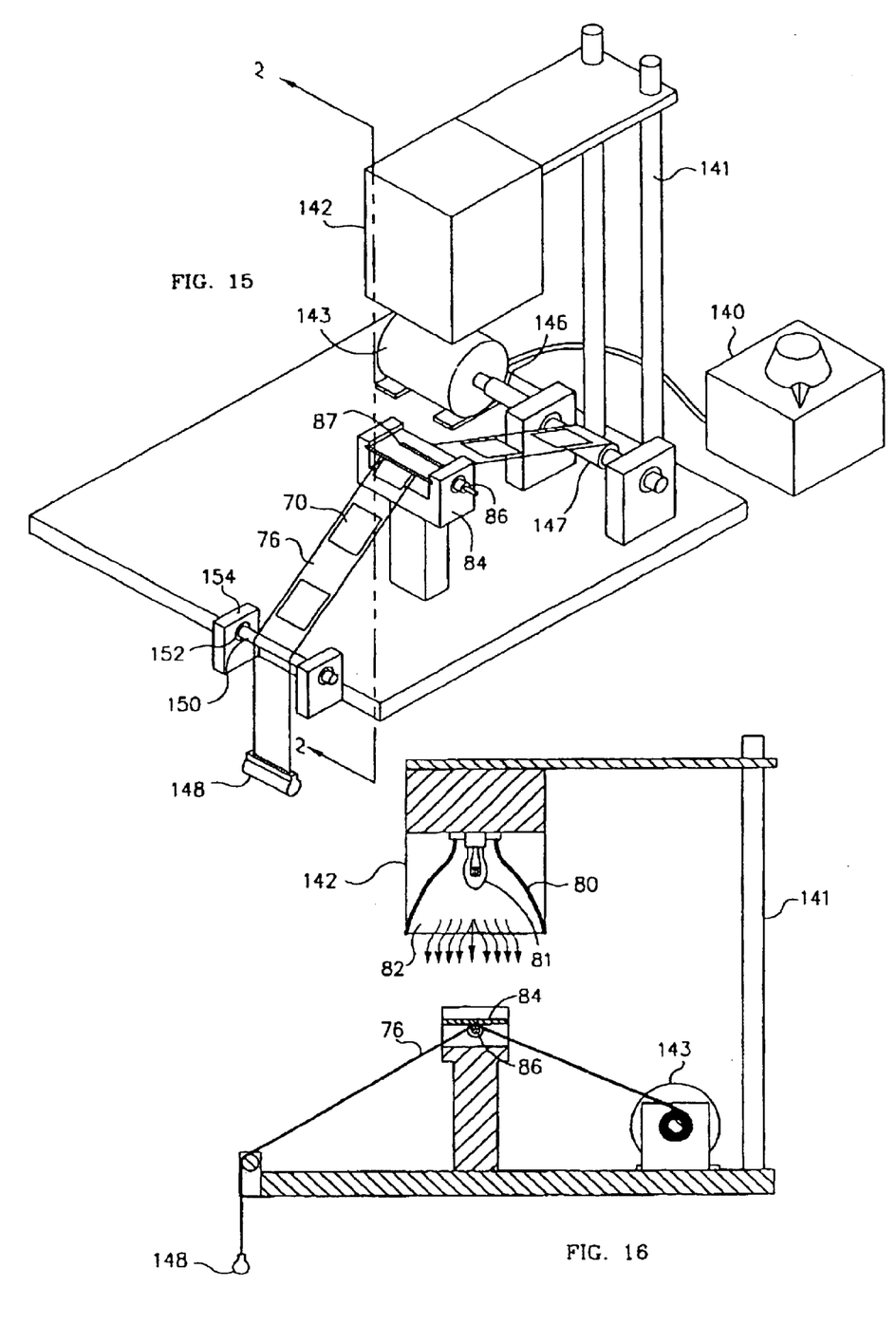
FIG. 15 is a perspective view of the apparatus used in the present invention stent fabrication process.
FIG. 16 is a cross-sectional view of the apparatus as seen along line 2—2 in FIG. 14 showing the perspective view of the apparatus.

FIG. 15 is a simplified perspective view of the apparatus used in the present invention stent fabrication process. Mounted on a stage is a supporting means 141 for locating the enclosure 142 containing light source 82 over the Y shaped regulating platform 84. The light source has a wavelength within the range of 360 to 440 nanometers with a preferred wavelength of 390 nanometers. It can be appreciated by those skilled in the art that other wavelengths of light can be used with this apparatus to activate a photo-sensitive material responsive to that particular wavelength of light.

A series of repeating stent patterns or individual frames 70 are imprinted on a spool of film 147 which is engaged to rotating shaft 146. A motor 143 is engaged to and rotates the shaft 146 which speed is regulated by controller 140. Mounted also on the stage is regulating platform 84 which supports the coated tubular member 64 engaged to a rotatable shaft 86. The top of the regulating platform comprises a plate which is mounted within two horizontal inward facing slots cut into regulating platform 84. The top contains a specifically configured centering slit 87 positioned over the film 76 and coated tubular member 64. The function of the configured slit is to act as a slit lens and center the UV light obtained from the light source onto the narrow region of the film. In this simplified example of the apparatus, the film engages the tubular member 64 which is free to rotate on shaft 86. The movement of the photographic film over the tubular member 64 generates a rotational force which is in unison with the advancement of the film. An alternate method not shown would be to use a synchronized motor mechanism that would control both the advancement of the film and the corresponding rotation of the tubular member. Also not shown is a means to automatically remove the exposed tubular member 92 from the regulating platform and replacing with a coated tubular member 64. The automatic mechanism needs to correspond with the movement of the film to replace the tubular member between individual stent patterns (frames) 70.

Mounted on the side of the stage is another supporting means 154 containing a rotatable shaft 150 supported by bearings 152. A weight is suspended from the end of the photographic film 148 and functions to provide tension on the photographic film to ensure adequate engagement with coated tubular member 64. A take-up reel or any number of tensioning mechanisms can suffice for the weight 148.

FIG. 16 is a cross-sectional view of the apparatus as seen along line 2—2 in FIG. 15 showing the perspective view of the apparatus. This cross-sectional view shows the relative position of UV light source 82 over regulating platform 84, slit 87 and tubular member 64. It can be seen from this figure that weight 148 provides tension to maintain the engagement of the photographic film to the tubular member.

Figures 17, 18:
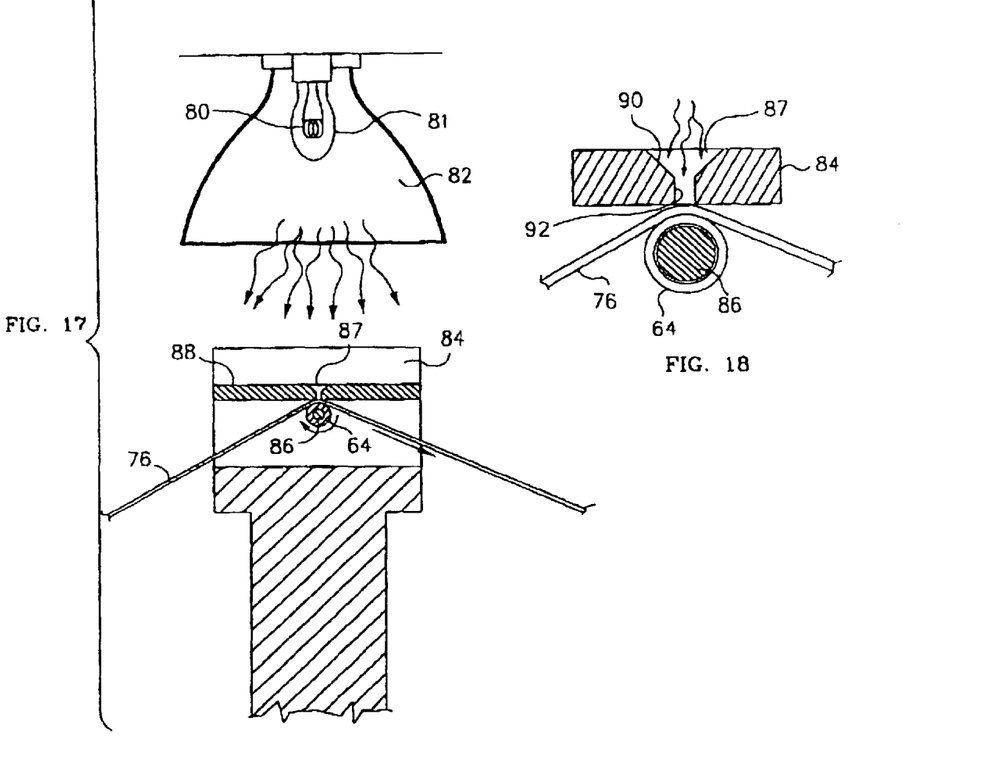
FIG. 17 is a cross-sectional view of the light source and the regulating platform.
FIG. 18 is a cross-sectional enlargement of the regulating platform of the apparatus.

FIG. 17 is a cross-sectional view of the light source and the regulating platform. This view demonstrates the orientation of the light source 82 facing in the general direction of the regulating platform 84. Diffuse UV light (shown by the arrows emanating from the light source) enter into specially configured slit 87. The figure also demonstrates one embodiment of the apparatus where the forward advancement of the photographic film 76 (shown by arrow) generates a rotational force (shown as clockwise) on the coated tubular member 64 which moves in unison with the film.

FIG. 18 is a cross-sectional enlargement of the regulating platform of the apparatus, specifically demonstrating the configuration of the focusing slit 87. Light enters beveled angles 90 which funnels the electromagnetic energy into a narrow channel 92 finally engaging photographic film 76. The pattern imprinted on the film blocks some of the light rays; while spaces in the pattern allow light to reach and react with the photo-sensitive resist on the coated tubular member 64. This process transfers the stent pattern from the relatively flat photographic film to the circular tubular member.

Figure 19:
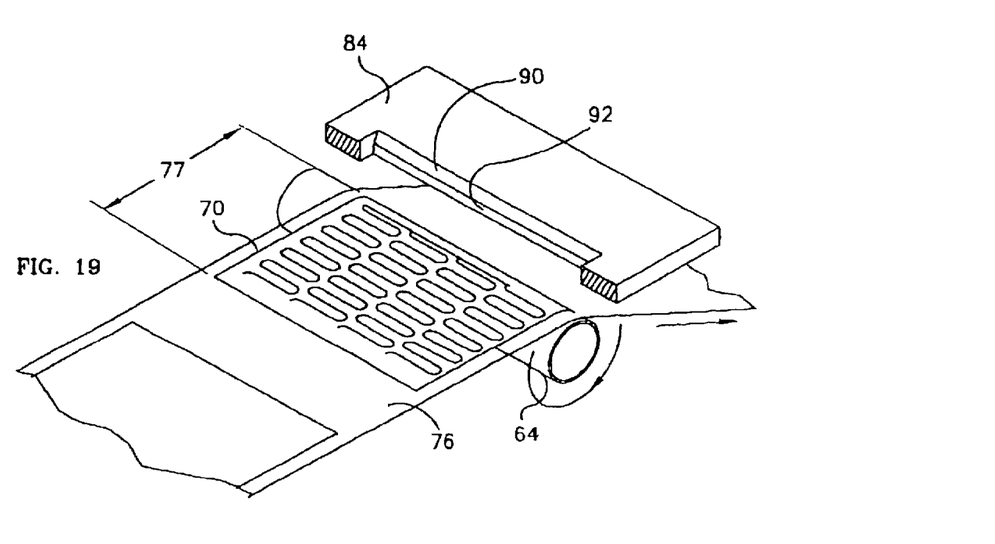
FIG. 19 is a perspective view of the regulating platform.

FIG. 19 is a side perspective view of the regulating platform. This figure shows a section of regulating platform 84, depicting one of the beveled angles 90 and one side of the narrow channel 92 of slit 87. Also demonstrated is that the width of beveled angle 90 and channel 92 is approximately equivalent to the width of the photographic film 76. Also shown is the photographic film 76 engaged with coated tubular member 64. Length 77 of frame 70 is designed and calibrated to equal the circumference of tubular member 64.

It is to be appreciated by persons skilled in the art that the present invention is not limited to what has been particularly shown and described hereinabove. Rather the scope of the present invention is defined only by the claims which follow:

I claim:
1. A stent fabrication method comprising the steps of:
(a) coating an outer surface of a metallic tubular member with a photo-sensitive resist resulting in a coated tubular member, said metallic tubular member having an outside surface, an inside surface and an inner lumen;
(b) placing said coated tubular member in an apparatus which simultaneously exposes a selected portion and shields other selected portions of said outer surface of said coated tubular member to a light source, yielding a partially exposed tubular member;
(c) immersing said partially exposed tubular member in said photo-resist developer resulting in a treated tubular member;
(d) sealing said inner lumen; and
(e) processing said treated tubular member by a chemical or electro-chemical etching process to remove metal located in said selected portions of said tubular member.

2. A stent fabrication method as recited in claim 1, further comprising the step of processing said tubular member with a plasma etch treatment prior to the step of coating said outer surface of said metallic tubular member with said photo-sensitive resist.

3. A stent fabrication method as recited in claim 1, further comprising the step of coating said outer surface of said tubular member with a coupling agent prior to the step of coating said outer surface of said metallic tubular member with said photo-sensitive resist.

4. A stent fabrication method as recited in claim 1, further comprising the step of incubating said treated tubular member in a temperature range, said temperature range being between 100 and 400 degrees Celsius, after the step of immersing said partially exposed tubular member to said negative resist developer.

5. A stent fabrication method as recited in claim 1, wherein said exposure of said light source to portions of said coated tubular member is regulated by a pattern imprinted on photographic film.

6. A stent fabrication method as recited in claim 2, further comprising the step of heating said tubular member in a temperature range, said temperature range being between 100 and 200 degrees Celsius, after the step of cleaning the tubular member.

7. A stent fabrication method as recited in claim 1, wherein said light source has a wavelength within the range of 360 to 440 nanometers.

8. A stent fabrication method as recited in claim 1, wherein said light source has a preferred wavelength optimized for the specific photoresist employed.

9. A stent fabrication method as recited in claim 3, wherein said coupling agent comprises a class of organosilane compounds.

10. A stent fabrication method as recited in claim 1, wherein a plurality of stents are made from a single piece of tubing.

11. A stent fabrication method as recited in claim 1, wherein said tubular member is made from a material selected from the group consisting of polymers, stainless steel, titanium, platinum, gold alloys, gold/platinum alloys, and tantalum.

12. A stent fabrication method as recited in claim 1, wherein said electro-chemical etching process employs a solution of phosphoric acid and sulfuric acid.

13. A stent fabrication method as recited in claim 1, wherein said electro-chemical etching process employs a solution of ferric chloride.

14. A stent fabrication method as recited in claim 1, wherein said electro-chemical etching process employs a solution of potassium cyanide.

15. A stent fabrication method as recited in claim 1, wherein said electro-chemical etching process employs a solution of sodium hypochloride.

16. A stent fabrication method as recited in claim 1, wherein said electro-chemical etching process employs a solution of hydrochloric acid and nitric acid.

17. A stent fabrication method comprising the steps of:
(a) coating an outer surface of a metallic tubular member with a photo-sensitive resist resulting in a coated tubular member, said metallic tubular member having an outside surface, an inside surface, and an inner lumen;
(b) placing said coated tubular member in an apparatus which simultaneously rotates said coated tubular member in conjunction with an advancing photographic film which regulates the exposure of a selected portions and shields other selected portion of said outer surface of said coated tubular member to a light source, yielding a partially exposed tubular member;
(c) immersing said partially exposed tubular member in a negative resist developer resulting in a treated tubular member;
(d) sealing said inner lumen; and
(e) processing the treated tubular member by chemical etching to remove a portion of uncovered metal.

18. A stent fabrication method as recited in claim 17, further comprising the step of processing said tubular member with a plasma etch treatment prior to the step of coating said outer surface of said metallic tubular member with said photo-sensitive resist.

19. A stent fabrication method as recited in claim 17, further comprising the step of coating said outer surface of said tubular member with a coupling agent prior to the step of coating said outer surface of said metallic tubular member with said photo-sensitive resist material.

20. A stent fabrication method as recited in claim 18, further comprising the step of incubating said treated tubular member in a temperature range, said temperature range being between 100 and 400 degrees Celsius, after the step of immersing said partially exposed tubular member to the negative resist developer.

21. A stent fabrication method as recited in claim 18, wherein said exposure of light source to portions of the stent is regulated by a stent configuration on transparent photographic film.

22. A stent fabrication method as recited in claim 19, further comprising the step of heating said tubular member in a temperature range, said temperature range being between 100 and 200 degrees Celsius, after the step of cleaning the tubular member.

23. A stent fabrication method as recited in claim 18, wherein said light source has a wavelength within the range of 360 to 440 nanometers.

24. A stent fabrication method as recited in claim 18, wherein said light source has a preferred wavelength optimized for the specific photoresist employed.

25. A stent fabrication method as recited in claim 19, wherein said coupling agent comprises a class of organo-silane compounds.

26. A stent fabrication method as recited claim 17, wherein a plurality of stents are made from a single piece of tubing.

27. A stent fabrication method as recited in claim 17, wherein said tubular member is made from a material selected from the group consisting of polymers, stainless steel, titanium, platinum, gold alloys, gold/platinum alloys, and tantalum.

28. A stent fabrication method as recited in claim 17, wherein said chemical etching process employs a solution of phosphoric acid and sulfuric acid.

29. A stent fabrication method as recited in claim 17, wherein said chemical etching process employs a solution of ferric chloride.

30. A stent fabrication method as recited in claim 17, wherein said chemical etching process employs a solution of potassium cyanide.

31. A stent fabrication method as recited in claim 17, wherein said chemical etching process employs a solution of sodium hypochloride.

32. A stent fabrication method as recited in claim 17, wherein said chemical etching process employs a solution of hydrochloric acid and nitric acid.

33. A stent fabrication method comprising the steps of:
(a) coating an outer surface of a metallic tubular member with a protective polymeric coating resulting in a coated tubular member, said metallic tubular member having an outside surface, an inside surface, and an inner lumen;
(b) placing said coated tubular member in an apparatus which simultaneously exposes a selected portion and shields other selected portions of said outer surface of said coated tubular member to a light source, resulting in some polymeric coating exposed and some polymeric coating unexposed, yielding a partially exposed tubular member;
(c) immersing said partially exposed tubular member in a solvent for selectively removing unexposed polymeric coating resulting in a treated tubular member;
(d) sealing said inner lumen; and
(e) processing said treated tubular member by chemical etching process to remove metal located in said selected portions of said tubular member.

34. A stent fabrication method as recited in claim 33, wherein said protective polymeric coating comprises a class of photo-sensitive resists.

35. A stent fabrication method as recited in claim 33, wherein said solvent for selectively removing unexposed polymeric coating comprises a class of negative resist developers.

36. A stent fabrication method as recited in claim 33, further comprising the step of cleaning said tubular member prior to the step of coating said outer surface of said metallic tubular member with said protective polymeric coating.

37. A stent fabrication method as recited in claim 33, further comprising the step of coating said outer surface of said tubular member with a coupling agent prior to the step of coating said outer surface of said metallic tubular member with said protective polymeric coating.

38. A stent fabrication method as recited in claim 33, further comprising the step of incubating said treated tubular member in a temperature range, said temperature range being between 100 and 400 degrees Celsius, after the step of immersing said partially exposed tubular member to said solvent for selectively removing unexposed polymeric coating.

39. A stent fabrication method as recited in claim 33, wherein said exposure of said light source to portions of said coated tubular member is regulated by a pattern imprinted on photographic film.

40. A stent fabrication method as recited in claim 33, further comprising the step of heating said tubular member in a temperature range, said temperature range being between 100 and 200 degrees Celsius, after the step of cleaning the tubular member.

41. A stent fabrication method as recited in claim 33, wherein said light source has a wavelength within the range of 360 to 440 nanometers with a preferred wavelength of 390 nanometers.

42. A stent fabrication method as recited in claim 33, wherein said light source has a preferred wavelength optimized for the specific photoresist employed.

43. A stent fabrication method as recited in claim 33, wherein said coupling agent comprises a class of organo-silane compounds.

44. A stent fabrication method as recited claim 33, wherein a plurality of stents are made from a single piece of tubing.

45. A stent fabrication method as recited in claim 33, wherein said tubular member is made from a material selected from the group consisting of polymers, stainless steel, titanium, platinum, gold alloys, gold/platinum, alloys and tantalum.

46. A stent fabrication method as recited in claim 33, wherein said electro-chemical etching process employs a solution of phosphoric acid and sulfuric acid.

47. A stent fabrication method as recited in claim 33, wherein said electro-chemical etching process employs a solution of ferric chloride.

48. A stent fabrication method as recited in claim 33, wherein said electro-chemical etching process employs a solution of potassium cyanide.

49. A stent fabrication method as recited in claim 33, wherein said electro-chemical etching process employs a solution of sodium hypochloride.

50. A stent fabrication method as recited in claim 33, wherein said electro-chemical etching process employs a solution of hydrochloric acid and nitric acid.

\* \* \* \* \*